US008386050B2

(12) United States Patent
Donoghue et al.

(10) Patent No.: US 8,386,050 B2
(45) Date of Patent: Feb. 26, 2013

(54) CALIBRATION SYSTEMS AND METHODS FOR NEURAL INTERFACE DEVICES

(75) Inventors: John P. Donoghue, Providence, RI (US); J. Christopher Flaherty, Topsfield, MA (US); Mijail D. Serruya, Providence, RI (US); Abraham H. Caplan, Cambridge, MA (US); Maryam Saleh, Chicago, IL (US); Kirk F. Korver, Salt Lake City, UT (US); Almut Branner, Salt Lake City, UT (US)

(73) Assignee: BrainGate Co., LLC, Ponte Vedra Beach, FL (US)

( * ) Notice: Subject to any disclaimer, the term of this patent is extended or adjusted under 35 U.S.C. 154(b) by 553 days.

(21) Appl. No.: 12/285,886

(22) Filed: Oct. 15, 2008

(65) Prior Publication Data

US 2010/0063411 A1 Mar. 11, 2010

Related U.S. Application Data

(63) Continuation of application No. 10/978,818, filed on Nov. 2, 2004, now abandoned.

(60) Provisional application No. 60/519,047, filed on Nov. 9, 2003.

(51) Int. Cl.
*A61N 1/3605* (2006.01)
*A61B 5/04001* (2006.01)
*A61B 5/0422* (2006.01)

(52) U.S. Cl. ............................ 607/62; 600/378; 600/381

(58) Field of Classification Search .................... 607/62; 600/378, 381

See application file for complete search history.

(56) References Cited

U.S. PATENT DOCUMENTS

| | | | |
|---|---|---|---|
| 5,092,329 A | 3/1992 | Graupe et al. | |
| 5,121,747 A | 6/1992 | Andrews | |
| 5,325,862 A | 7/1994 | Lewis et al. | |
| 5,476,441 A | 12/1995 | Durfee et al. | |
| 5,645,059 A | 7/1997 | Fein et al. | |
| 5,938,689 A | 8/1999 | Fischell et al. | |
| 6,171,239 B1 * | 1/2001 | Humphrey | 600/372 |
| 7,010,351 B2 | 3/2006 | Firlik et al. | |
| 7,162,305 B2 | 1/2007 | Tong et al. | |
| 7,212,851 B2 | 5/2007 | Donoghue et al. | |
| 7,280,870 B2 | 10/2007 | Nurmikko et al. | |
| 7,346,396 B2 | 3/2008 | Barriskill et al. | |
| 7,381,192 B2 | 6/2008 | Brodard et al. | |
| 7,392,079 B2 | 6/2008 | Donoghue et al. | |
| 2002/0077534 A1 | 6/2002 | DuRousseau | |
| 2002/0082514 A1 | 6/2002 | Williams et al. | |
| 2003/0139782 A1 | 7/2003 | Duncan et al. | |
| 2003/0139783 A1 | 7/2003 | Kilgore et al. | |
| 2003/0149678 A1 * | 8/2003 | Cook | 706/46 |
| 2003/0158587 A1 * | 8/2003 | Esteller et al. | 607/45 |
| 2005/0090756 A1 | 4/2005 | Wolf et al. | |
| 2005/0137652 A1 | 6/2005 | Cauller et al. | |
| 2005/0182341 A1 | 8/2005 | Katayama et al. | |
| 2005/0273890 A1 | 12/2005 | Flaherty et al. | |
| 2006/0049957 A1 | 3/2006 | Surgenor et al. | |
| 2006/0149338 A1 | 7/2006 | Flaherty et al. | |
| 2006/0167371 A1 | 7/2006 | Flaherty et al. | |

(Continued)

*Primary Examiner* — Nicole F Lavert
(74) *Attorney, Agent, or Firm* — SoCal IP Law Group LLP; M. Kala Sarvaiya; Steven C. Sereboff

(57) ABSTRACT

A system and method for a neural interface system with integral calibration elements may include a sensor including a plurality of electrodes to detect multicellular signals, an interface to process the signals from the sensor into a suitable control signal for a controllable device, such as a computer or prosthetic limb, and an integrated calibration routine to efficiently create calibration output parameters used to generate the control signal. A graphical user interface may be used to make various portions of the calibration and signal processing configuration more efficient and effective.

18 Claims, 5 Drawing Sheets

U.S. PATENT DOCUMENTS

| | | |
|---|---|---|
| 2006/0167530 A1 | 7/2006 | Flaherty et al. |
| 2006/0189900 A1 | 8/2006 | Flaherty |
| 2006/0195042 A1 | 8/2006 | Flaherty |
| 2006/0206167 A1 | 9/2006 | Flaherty et al. |
| 2006/0241356 A1 | 10/2006 | Flaherty |
| 2006/0253166 A1 | 11/2006 | Flaherty et al. |
| 2007/0032738 A1 | 2/2007 | Flaherty et al. |
| 2007/0156126 A1 | 7/2007 | Flaherty |
| 2010/0023021 A1 | 1/2010 | Flaherty |
| 2010/0063411 A1 | 3/2010 | Donoghue et al. |

* cited by examiner

CALIBRATION SYSTEMS AND METHODS FOR NEURAL INTERFACE DEVICES

This is a continuation of application Ser. No. 10/978,818, filed Nov. 2, 2004, now abandoned which is incorporated herein by reference and claims the benefit of priority under 35 U.S.C. §119(e) of U.S. Provisional Application No. 60/519,047, filed Nov. 9, 2003.

DESCRIPTION OF THE INVENTION

1. Field of the Invention

The present invention relates to systems and methods for calibrating neural interface devices, and, more particularly, to calibration systems and methods for neural interface devices employing mufti-electrode sensors for detecting neuronal activity.

2. Description of Related Art

Neural interface devices are currently under development for numerous applications involving restoration of lost function due to traumatic injury or neurological disease. Sensors, such as electrode arrays, implanted in the higher brain regions that control voluntary movement can be activated voluntarily to generate electrical signals that can be processed by a neural interface device to create a thought invoked control signal. Such control signals can be used to control numerous devices including computers and communication devices, external prostheses, such as an artificial arm or functional electrical stimulation of paralyzed muscles, as well as robots and other remote control devices. Patient's afflicted with amyotrophic lateral sclerosis (Lou Gehrig's Disease), particularly those in advanced stages of the disease, would also be applicable to receiving a neural interface device, even if just to improve communication to the external world and thus improve their quality of life.

Early attempts to utilize signals directly from neurons to control an external prosthesis encountered a number of technical difficulties. The ability to identify and obtain stable electrical signals of adequate amplitude was a major issue. Another problem that has been encountered is caused by the changes that occur to the neural signals that occur over time, resulting in a degradation of system performance. Neural interface systems that utilize other neural information, such as electrocorticogram (ECOG) signals, local field potentials (LFPs) and electroencephalogram (EEG) signals have similar issues to those associated with individual neuron signals. Since all of these signals result from the activation of large groups of neurons, the specificity and resolution of the control signal that can be obtained is limited. However, if these lower resolution signals could be properly identified and the system adapt to their changes over time, simple control signals could be generated to control rudimentary devices or work in conjunction with more the higher power control signals processed directly from individual neurons.

There is therefore a need for an improved neural interface system which incorporate various novel elements needed to perform an efficient and effective calibration routine which can identify the optimal multicellular signals to be processed, and adjust for the natural changes in those signals that occur over time. Performance of the calibration routine at the outset and repeated periodically throughout the life of the system would ensure a sophisticated and effective control signal for the long term control of an external device.

SUMMARY OF THE INVENTION

According to a first aspect of the invention, a neural interface system is disclosed. The neural interface system collects multicellular signals emanating from the central nervous system of a patient and transmits processed signals to a controlled device. The system comprises a sensor for detecting multicellular signals, the sensor consisting of a plurality of electrodes. The electrodes are designed to allow chronic detection of multicellular signals. An interface is designed to receive the multicellular signals from the sensor and process the multicellular signals to produce processed signals. The processed signals are transmitted from the interface to a controlled device. Integrated into the system is a calibration routine, which generates one or more calibration output parameters used by the interface to produce the processed signal. The integrated calibration routine may be performed by an operator at least one time during the use of the system.

The operator, a qualified individual in the use of the calibration routine, utilizes calibration apparatus to generate the calibration output parameters. The calibration apparatus can have certain functions integrated into the interface of the system, or may be a stand alone apparatus that communicates with the interface. The calibration apparatus can be physically connected to the interface via an electromechanical cable, or can communicate via wireless technologies. The calibration routine can be performed with or without patient involvement. Patient involvement may include having the patient imagine particular events such as imagined movement, memory recall, imagined states or other imaginable events.

The controlled device of an exemplary embodiment is an assistive device for a patient with a paralyzed or otherwise reduced function due to traumatic injury or neurological disease. In a preferred embodiment, the multicellular signals include, at a minimum, neuronal spikes sensed with a mufti-electrode array implanted in the motor cortex portion of the patient's brain.

In another aspect, the system includes one or more safety checks regarding successful completion of the calibration routine. For example, the operator is qualified by performing a mock calibration utilizing data included in the calibration apparatus, either synthetic data or previously recorded human data. Alternatively or additionally, operator secured access is provided preventing inadvertent or malicious changes in calibration being performed by improper or unqualified individuals.

In still another aspect, multiple calibration routines are embedded in the system. The multiple routines can be utilized for comparative purposes, routines can be specific to a particular controlled device and can differentiate an initial calibration from subsequent calibration. In a preferred embodiment, multiple calibration routines are performed, and a check is performed to select the best performance. In one embodiment, specific calibration routines are linked to specific controlled devices. In still another embodiment, the neural interface system includes one or more initial calibration routines, and one or more subsequent calibration routines. The subsequent calibration routines have a reduced number of steps resulting in reduced calibration duration, and may utilize data captured from previous calibrations including date from the initial calibration.

In some aspects, the calibration routine includes preset limits for either input variables or output variables of the calibration routine. In one embodiment, these limits are adjustable by a subset of potential operators, such as only by the clinician. This tiered approach offers the potential of both safe and efficient calibration of the system, allowing less qualified operators to make fine adjustments only.

In an aspect, certain parameters of the calibration routine are varied automatically based on the quality and quantity of neural signals detected. An iterative process is created to efficiently select the best signals for processing based on the patient and the requirements of the system, especially as they relate to the requirements of the particular controlled device. For example, particular targets for number of multicellular signals may be linked with the specific controlled device intended for use. The calibration routine can automatically readjust parameters based on surpassing or underachieving the target signal amount, and calibration repeated to select the most appropriate signals.

In some aspects, the calibration apparatus includes internal safety checks for proper calibration. The system can check for performance and other requirements, and if below a particular level, the system can enter certain states. Such states may include an alarm or warning condition, or a lockout condition wherein a repeat calibration or other action is required prior to transmitting the control signals to the controlled device.

According to another aspect of the invention, a method of calibrating a neural interface system is disclosed. The method includes providing a neural interface system for collecting multicellular signals emanating from the central nervous system of a patient and for transmitting processed signals to a controlled device. The neural interface system includes a sensor for detecting the multicellular signals. The sensor consists of a plurality of electrodes that detect the multicellular signals. An interface receives the multicellular signals from the sensor and processes the signals to generate a processed signal which is sent to a controlled device. The method further includes the performance by an operator of a calibration routine, at least one time during the use of the system. The calibration routine produces one or more calibration output parameters to be used by the system to generate the processed signals.

According to another aspect of the invention, a neural signal processing unit is disclosed. The neural signal processing unit comprises an input port for multiple neural signal input and a graphical user interface. The graphical user interface includes: a display monitor for displaying information from multiple individual neural signals and an input device for selecting graphical representations of neural signals and graphical representations of parameter values on the display monitor. The multiple neural signals can be selected with the input device and properties associated multiple individual neural signals can be changed simultaneously.

According to another aspect of the invention, another neural signal processing unit is disclosed. The neural signal processing unit comprises an input port for multiple neural signal input and a graphical user interface. The graphical user interface includes: a display monitor for displaying information from multiple individual neural signals and an input device for selecting graphical representations of neural signals and graphical representations of parameter values on the display monitor. One or more neural signals can be viewed automatically by selecting a graphical representation of a specific parameter value.

According to another aspect of the invention, another neural signal processing unit is disclosed. The neural signal processing unit comprises an input port for multiple neural signal input and a graphical user interface. The graphical user interface includes a display monitor for displaying information from multiple individual neural signals and an input device for selecting graphical representations of neural signals and graphical representations of parameter values on the display monitor. One or more neural signals can have a parameter changed by moving the graphical representation of the neural signal to the location of a graphical representation of a specific parameter value or by moving a graphical representation of a specific parameter value to a location of a graphical representation of the neural signal.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate various embodiments of the present invention, and, together with the description, serve to explain the principles of the invention.

DESCRIPTION OF THE EMBODIMENTS

Reference will now be made in detail to the present embodiments of the invention, examples of which are illustrated in the accompanying drawings. Wherever possible, the same reference numbers will be used throughout the drawings to refer to the same or like parts.

Systems and methods consistent with the invention detect neural signals generated within a patient's body and implement various signal processing techniques to generate processed signals for transmission to a device to be controlled. In one exemplary environment, a neural interface system includes a calibration routine which is implemented to ensure optimal, long term control of the controlled device. Numerous preferred embodiments of calibration routines are described, enabling the neural interface system to efficiently work with various controlled devices, such as prosthetic limbs, robots and robotic machinery, and computer control devices. The various calibration routines described also allow the neural interface system to be compatible with a broad based patient population with varied level of neural signal quality. Subsequent calibrations may be performed to adjust for changes in signal quality and other changes, providing for effective long term, or chronic use of the system. In other exemplary embodiments, improved user interface systems are described, allowing an operator to create processed signals in an expeditious, efficient manner.

Figure 1:
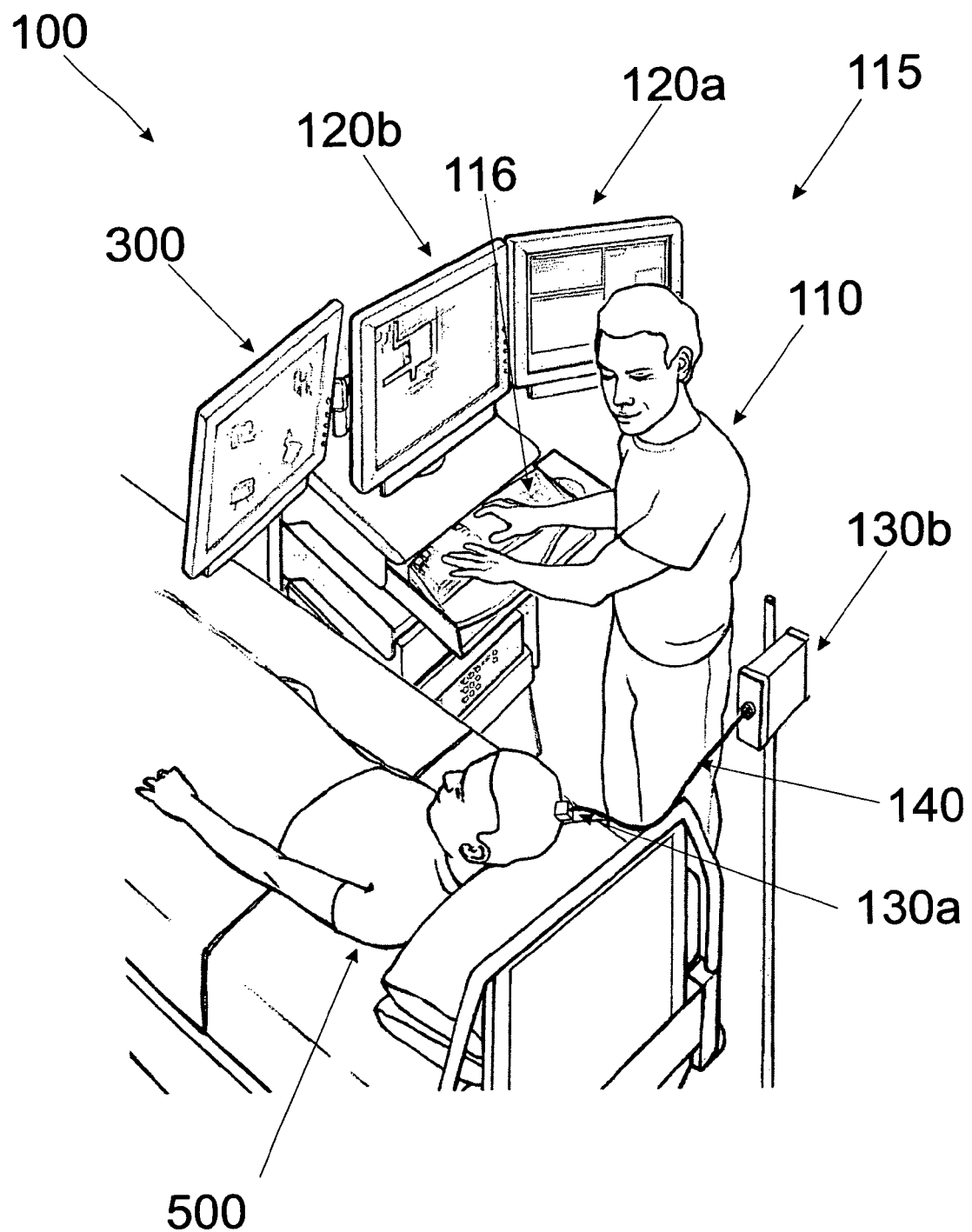
FIG. 1 illustrates a neural interface system consistent with the present invention.

FIG. 1 shows a neural interface system 100 of implanted components and components external to the body of a patient 500. A sensor for detecting multicellular signals, such as a two dimensional array of multiple protruding electrodes, may be implanted in the brain of patient 500, in an area such as the motor cortex. Alternatively, the sensor may include one or more wires or wire bundles which include a plurality of electrodes. Patient 500 may be a patient with a spinal cord injury or afflicted with a neurological disease that has resulted in a loss of voluntary control of various muscles within the patient's body. The various electrodes of the sensor detect multicellular signals, such as neuron spikes which emanate from the individual neurons of the brain. The sensor can be placed at one or more various locations within the body of patient 500, such as at an extracranial site, preferably in a location to collect multicellular signals directly from the central nervous system. The sensor can be placed on the surface of the brain without penetrating, such as to detect local field potential signals, or on the scalp to detect electroencephalogram (EEG) signals.

The sensor electrodes of system 100 can be used to detect various multicellular signals including neuron spikes, electrocorticogram signals (ECoG), local field potential signals, etectroencelphalogram (EEG) signals and other multicellular signals. The electrodes can detect multicellular signals from clusters of neurons and provide signals midway between single neuron and electroencephalogram recordings. Each electrode is capable of recording a combination of signals, including a plurality of neuron spikes.

As shown in FIG. 1, an interface may comprise first interface portion 130A and second interface portion 130B. The interface may receive the multicellular signals from the sensor and perform various signal processing functions including but not limited to amplification, filtering, sorting, conditioning, translating, interpreting, encoding, decoding, combining, extracting, mathematically transforming, and/or otherwise processing those signals to generate a control signal for transmission to a controlled device. The interface may comprise multiple components as shown in FIG. 1, or a single component. Each of the interface components can be implanted in patient 500 or be external to the body.

In FIG. 1, controlled device 300 is a computer system, and patient 500 may be controlling one or more of a mouse, keyboard, cursor, joystick or other computer input device. Numerous other controlled devices can be included in system 100, individually or in combination, including but not limited to prosthetic limbs, functional electrical stimulation (FES) devices and systems, robots and robotic components, teleoperated devices, computer controlled devices, communication devices, environmental control devices, vehicles such as wheelchairs, remote control devices, medical therapeutic and diagnostic equipment such as drug delivery apparatus and other controllable devices applicable to patients with some form of paralysis or diminished function, as well as any device that may be better utilized under direct brain or thought control.

The sensor is connected via a multi-conductor cable, not shown, to first interface portion 130A which includes a transcutaneous pedestal which is mounted to the patient's skull. The multi-conductor cable includes a separate conductor for each electrode, as well as additional conductors to serve other purposes. Various descriptions of the sensor and multi-conductor cable are described in detail in relation to subsequent figures included herebelow.

First interface portion 130A may include various signal conditioning elements such as amplifiers, filters, and signal multiplexing circuitry. First interface portion 130A is electrically attached to second interface portion 130B via intra-interface cable 140. Intra-interface cable 140, as well as other physical cables incorporated into system 100, may include electrical wires, optical fibers, other means of transmitting data and/or power and any combination of those. The number of individual conductors of intra-interface cable 140 can be greatly reduced from the number of conductors included in the multi-conductor cable between the implanted sensor and first interface portion 130A through signal combination circuitry included in first interface portion 130A. Intra-interface cable 140, as well as all other physical cables incorporated into system 100, may include shielding elements to prevent or otherwise reduce the amount of electromagnetic noise added to the various neural signals, processed neural signals and other signals carried by those cables. In an alternative preferred embodiment, intra-interface cable 140 is replaced with a wireless connection for transmission between first interface portion 130A and second interface portion 130B. Wireless communication means, well known to those of skill in the art, can be utilized to transmit information between any of the components of system 100.

A qualified individual, operator 110, performs a calibration of system 100 at some time during the use of system 100, preferably soon after implantation of the sensor. As depicted in FIG. 1, operator 110 utilizes calibration apparatus 115 which includes two monitors, first calibration monitor 120a and second calibration monitor 120b, along with calibration keyboard 116 to perform the calibration routine. The software programs and hardware required to perform the calibration can be included in the interface, such as second interface portion 130B, or in a central processing unit incorporated into calibration apparatus 115. Calibration apparatus 115 can include additional input devices, such as a mouse or joystick, not shown. Calibration apparatus 115 can include various elements, functions and data including but not limited to: memory storage for future recall of calibration activities, operator qualification routines, standard human data, standard synthesized data, neuron spike discrimination software, operator security and access control, controlled device data, wireless communication means, remote (such as via the internet) calibration communication means and other elements, functions and data used to provide an effective and efficient calibration on a broad base of applicable patients and a broad base of applicable controlled devices.

Operator 110 may be a clinician, technician, caregiver or even the patient themselves in some circumstances. Multiple operators may perform a calibration, and each operator may be limited by system 100, via passwords and other control configurations, to only perform specific functions. For example, only the clinician may be able to change specific critical parameters, or set upper and lower limits on other parameters, while a caregiver or the patient, may not be able to access those portions of the calibration procedure. The calibration procedure includes the setting of numerous parameters needed by the system 100 to properly control controlled device 300. The parameters include but are not limited to various signal conditioning parameters as well as selection of specific multicellular signals for processing to generate the device control. The various signal conditioning parameters include, but are not limited to, threshold levels for amplitude sorting and filtering levels and techniques.

The operator 110 may be required by system 100 to perform certain tasks, not part of the actual calibration, to be qualified and thus allowed to perform the calibration routine. The tasks may include analysis of pre-loaded multicellular signals, either of synthetic or human data, and may include previous data captured from patient 500. The mock analysis can be tested for accuracy, requiring a minimum performance for the calibration routine to continue.

The calibration routine will result in the setting of various calibration output parameters. Calibration output parameters may consist of but are not limited to: electrode selection, neural signal selection, neuron spike selection, electrocorticogram signal selection, local field potential signal selection, electroencephalogram signal selection, sampling rate by signal, sampling rate by group of signals, amplification by signal, amplification by group of signals, filter parameters by signal and filter parameters by group of signals. In an embodiment, at least one of the output parameters includes the selection of a subset of multicellular signals to be processed by the interface to generate the controlled device control signal. In an alternative embodiment, the calibration output parameters can only be set within preset limits. In another embodiment, the limits can be changed by any operator, and in a preferred embodiment, only operators with specific permissions, such as password controlled permissions, can change the limits for individual parameters.

The calibration routine may be performed soon after sensor implantation, and prior to control of controlled device 300. System 100 may include an internal lockout feature which prevents control of any controlled device, prior to successfully completing a calibration procedure. In the performance of the calibration routine, the operator 110 can perform multiple calibrations and compare results of each. Calibration routines may be performed on a periodic basis, and may include the selection and deselection of specific neural signals over time. The initial calibration routine may include initial values, or starting points, for one or more of the calibration output parameters. Subsequent calibration routines may involve utilizing previous calibration output parameters which have been stored in a memory storage element of system 100. Subsequent calibration routines may be shorter in duration than an initial calibration and may require less patient involvement. Subsequent calibration routine results may be compared to previous calibration results, and system 100 may require a repeat of calibration if certain comparative performance is not achieved.

The calibration routine may include the steps of (a) setting a preliminary set of calibration output parameters; (b) generating processed signals to control the controlled device; (c) measuring the performance of the controlled device control; and (d) modifying the calibration output parameters. The calibration routine may further include the steps of repeating steps (b) through (d). The order of the steps may be altered, as necessary. Additionally or alternatively, any of the steps (b) through (d) may be omitted.

In the performance of the calibration routine, the operator 110 may involve the patient 500 or perform steps that do not involve the patient. The operator 100 may have patient 500 think of an imagined movement, imagined state, or other imagined event, such as a memory, an emotion, the thought of being hot or cold, or other imagined event not necessarily associated with movement. The patient participation may include the use of one or more cues such as audio cues, visual cues, olfactory cues, and tactile cues. The patient 500 may be asked to imagine multiple movements, and the output parameters selected during each movement may be compared to determine an optimal set of output parameters. The imagined movements may include the movement of a part of the body, such as a limb, arm, wrist, finger, shoulder, neck, leg, ankle, and toe, and imagining moving to a location, moving at a velocity or moving at an acceleration.

The calibration routine may include classifying the multicellular signals into one or more of two groups: discrete data and continuous data. Numerous factors can be analyzed from the neural signals received such as firing rate, average firing rate, standard deviation in firing rate and other mathematical analyses of firing rate. Determining the maximum modulation of firing rate, such as through the use of fano factor techniques, may be desirable in selecting which neural signals to process, as well as which imagined movement is generating the most useful signals. For particular mathematical algorithms, such as linear filters used to transform the selected multicellular signals into the controlled device control signal, it may be desirous to have a minimum of seven (7) neural signals for optimal device control.

The calibration routine will utilize one or more calibration input parameters to determine the calibration output parameters. In addition to the multicellular signals themselves, system or controlled device performance criteria can be utilized. In order to optimize the system, an iterative analysis of modifying the performance criteria, based on the number of multicellular signals that meet the criteria versus the optimal number of multicellular signals to be included in the signal processing for the particular controlled device, can be performed. Criteria can be increased or decreased in the signal selection process during the calibration procedure.

Other calibration input parameters include various properties associated with the multicellular signals including one or more of: signal to noise ratio, frequency of signal, amplitude of signal, neuron firing rate, average neuron firing rate, standard deviation in neuron firing rate, modulation of neuron firing rate as well as a mathematical analysis of any signal property including modulation of any signal property. Additional calibration input parameters include but are not limited to: system performance criteria, controlled device electrical time constants, controlled device mechanical time constants, other controlled device criteria, types of electrodes, number of electrodes, patient activity during calibration, target number of signals required, patient disease state, patient condition, patient age and other patient parameters and event based (such as a patient imagined movement event) variations in signal properties including neuron firing rate activity.

The calibration routine may classify one or more multicellular signals into three or more classifications for subsequent selection for further processing into the processed signal for transmission to the controlled device. The multiple classifications can be completed in the initial portion of the calibration routine, resulting in a count of each class of available signal. Based on various requirements including the requirements of the control device and applicable mathematical transfer functions, signals can be selected from the most appropriate classification, or a different number of classification states can be chosen, and the signals may be reclassified in order to select the most appropriate signals for optimal device control.

It may be desirous for the calibration routine to exclude one or more multicellular signals based on a desire to avoid signals that respond to certain patient active functions, such as non-paralyzed functions, or even certain imagined states. The calibration routine may include having the patient imagine a particular movement or state and, based on sufficient signal activity such as firing rate or modulation of firing rate, excluding that signal from the signal processing based on that particular undesired imagined movement or imagined state. Alternatively, real movement accomplished by the patient may also be utilized to exclude certain multicellular signals emanating from specific electrodes of the sensor.

Figure 2:
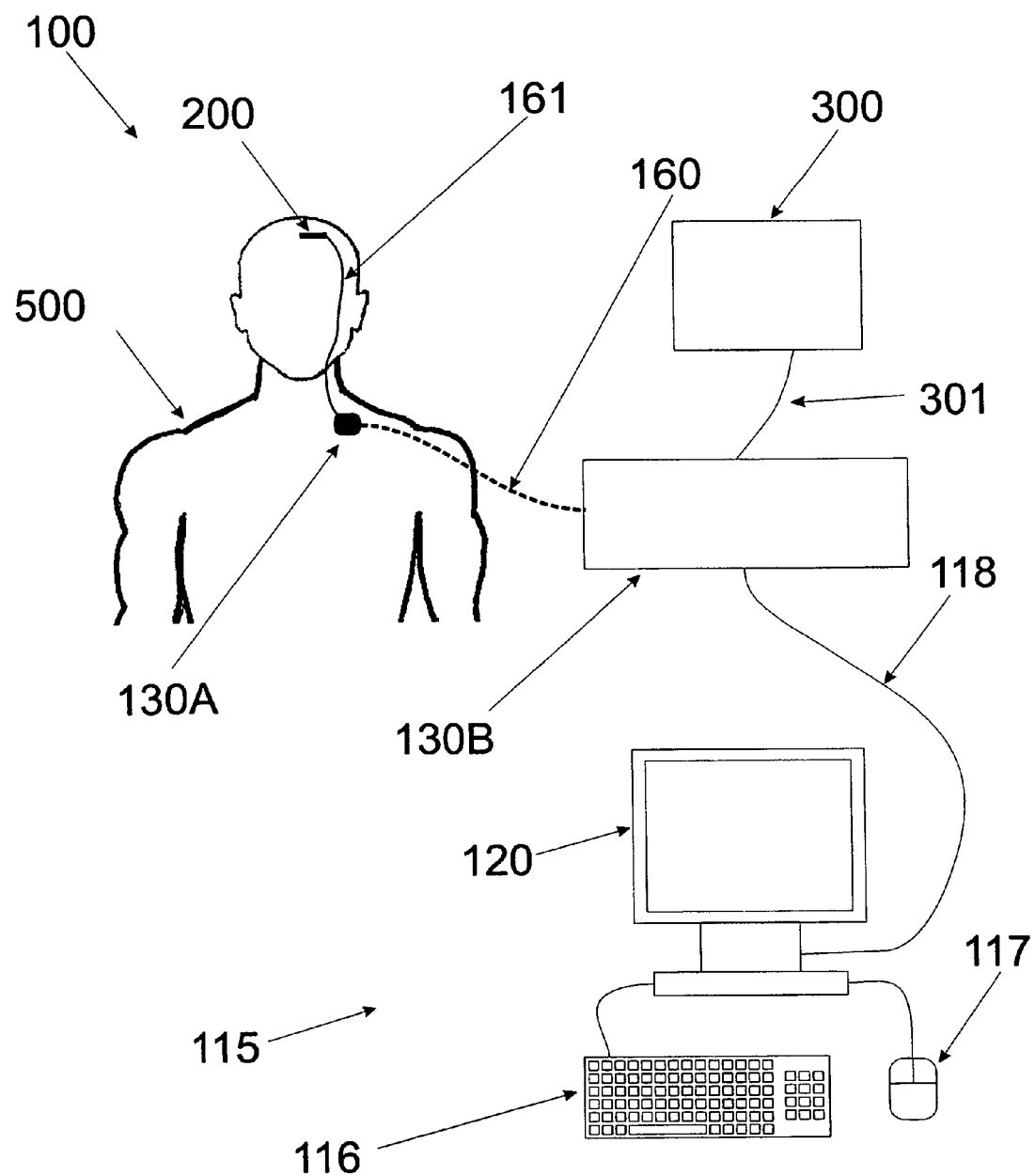
FIG. 2 illustrates an exemplary embodiment of a neural interface system consistent with the present invention.

Referring now to FIG. 2, system 100, according to another exemplary embodiment of the invention, is shown. Patient 500 has been implanted with sensor 200, preferably a multielectrode array placed in the motor cortex of patient 500's brain, however any arrangement of electrodes, such as wire electrodes, can be utilized and placed anywhere that multicellular activity can be recorded. The sensor 200 may be used to detect neuron spikes, or other multicellular signals. The sensor 200 may detect multiple spikes from a single electrode.

The sensor 200 is connected to first interfaces portion 130A, implanted within patient 500, via connecting cable 161. In a preferred embodiment, sensor 200 includes at least eighty (80) electrodes and connecting cable 161 is a multi-conductor flexible miniaturized cable including a conductor for each electrode, as well as other conductors. Alternatively, sensor 200 may include signal multiplexing circuitry allowing connecting cable 161 to include less than eighty conductors. In another alternative, a wireless connection could be integrated into sensor 200, sending signals through the skull to first interface portion 130A. First interface portion 130A is connected to second interface portion 130B, external to patient 500, via transcutaneous communication means 160 which could be either an electromechanical miniaturized cable designed to pass through the skin of the patient, or preferably transcutaneous communication means 160 is a wireless communication path accomplished by including wireless communication transmit and receive technology in both first interface portion 130A and second interface portion 130B. In an alternative embodiment, first interface portion 130A and second interface portion 130B are combined into a single unit, and the combined device may be implanted within patient 500, avoiding the need for transcutaneous communication means 160.

The interface, including first interface portion 130A, transcutaneous communication means 160, and second interface portion 130B, receives the multicellular signals from sensor 200, processes the multicellular signals to generate processed signals, and transmits the processed signals to the controlled device. First interface portion 130A may include various signal conditioning elements such as amplifiers, filters and signal multiplexing circuitry. Second interface portion 130B receives the modified multicellular signals from the first interface portion 130A and performs various signal processing functions including but not limited to amplification, filtering, sorting, conditioning, translating, interpreting, encoding, decoding, combining, extracting, mathematically transforming and/or otherwise processing those signals to generate a control signal for transmission to a controlled device. Second interface portion 130B may include various elements, functions and data to perform a calibration routine, such as those functions not already included in calibration apparatus 115. In a preferred embodiment, second interface portion 130B includes a memory storage unit that stores a complete history of all calibration information, which can be recalled to perform repeat and/or subsequent calibrations.

Second interface portion 130B is connected to controlled device 300 via controlled device cable 301. As described similarly throughout, controlled device cable 301 could be replaced with wireless communication means through the addition of wireless transmission capability into second interface portion 130B and wireless receiving capability into controlled device 300. In an embodiment, both receive and transmit technologies are included in both controlled device 300 and second interface portion 130B allowing feedback from controlled device 300 to second interface portion 130B to be used to improve system performance. Controlled device 300 can be a number of controllable devices, including a combination of controllable devices which are controlled by a single or multiple control signals which are generated by the second interface portion 130B. Lists of applicable controlled devices 300 have been described hereabove.

Calibration apparatus 115 includes calibration monitor 120, calibration keyboard 116 and calibration mouse 117. Calibration apparatus 115 is attached to second interface portion 130B via calibration connecting means 118, an electromechanical cable. However, it should be appreciated that calibration connecting means 118 could be replaced with wireless communication means included in calibration apparatus 115 and second interface portion 130B. The operator, not shown, would utilize calibration apparatus 115 at least one time in the calibration of system 100. The software programs and hardware required to perform the calibration can be included in the interface, such as second interface portion 130B, or be included in a central processing unit incorporated into calibration apparatus 115. Calibration apparatus 115 can include additional input devices, such as a joystick, not shown. Calibration apparatus 115 can include various elements, functions and data including but not limited to: memory storage for future recall of calibration activities, operator qualification routines, standard human data, standard synthesized data, neuron spike discrimination software, operator security and access control, controlled device data, wireless communication means, remote (such as via the internet) calibration communication means and other elements, functions and data used to provide an effective and efficient calibration on a broad base of applicable patients and a broad base of applicable controlled devices.

Figure 3:
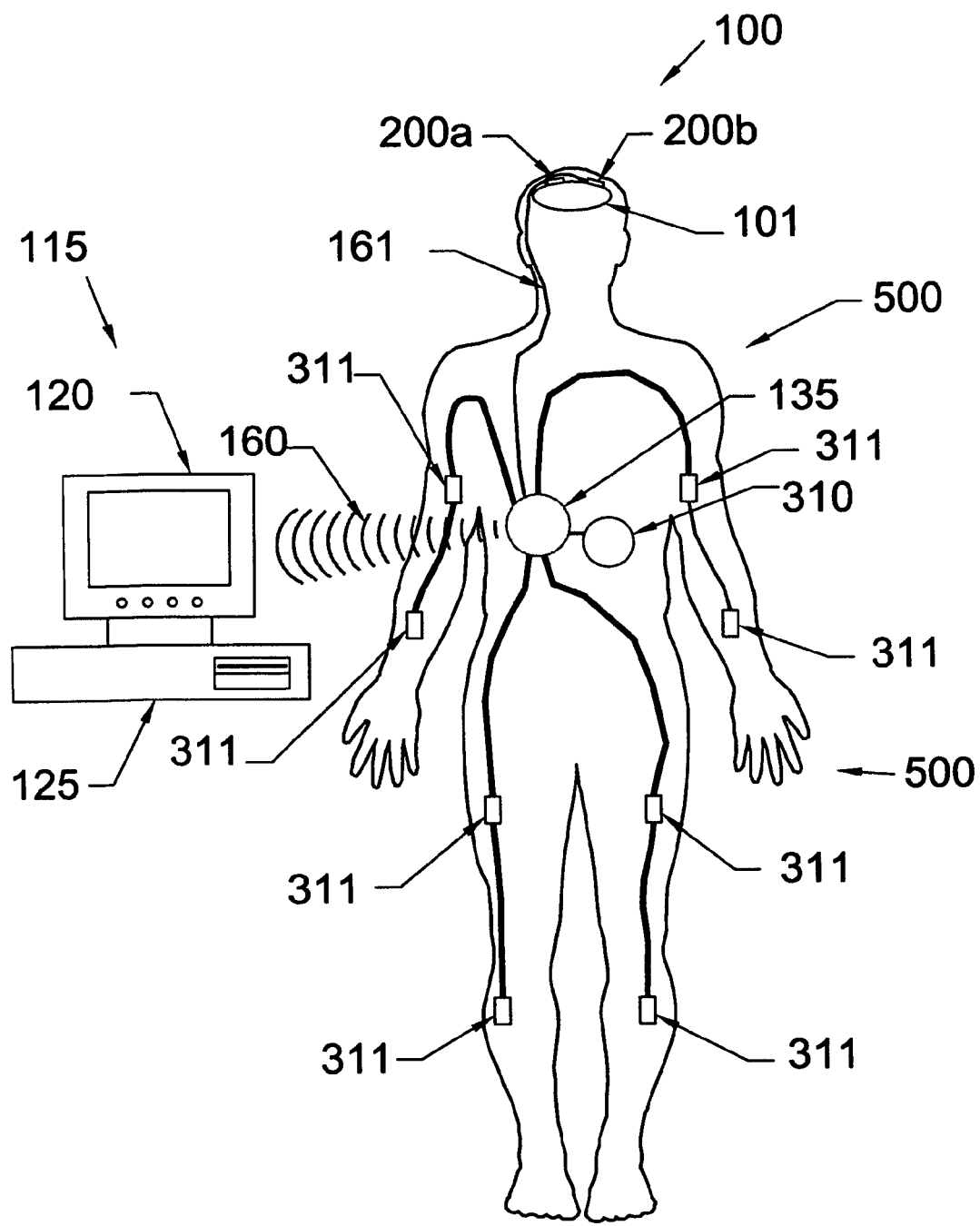
FIG. 3 illustrates another exemplary embodiment of a neural interface system consistent with the present invention.

In FIG. 3, system 100, according to still another exemplary embodiment of the invention, is shown, wherein two separate sensors, first sensor 200a and second sensor 200b are implanted in patient 500. While both sensors 200a and 200b are shown to be located in brain 101 of patient 500, at least one of the sensors may be placed in any location that can detect multicellular signals. Each of sensors 200a and 200b is attached via connecting cable 161 to central implant 135 which includes the interface portion of system 100, as well as other elements such as a power supply, wireless communication means, memory storage, central processing unit, physiologic and other sensor input ports, control signal output ports and other functions. Central implant 135 is connected to various other implants including a series of implants, implanted control devices 311 which could be Functional Electrical Stimulation (FES) devices, other control devices, sensory devices, or combination control and sensory devices. Also connected to central implant 135 is an implanted drug infusion device, such as implanted pump 310. The interface portion of central implant 135 may produce multiple control signals to control multiple devices with different functions such as implanted controlled devices 311, preferable an FES device, as well as a drug delivery device (e.g., implanted pump 310).

Also depicted in FIG. 3 is calibration apparatus 115 which includes calibration monitor 120 and external equipment means 125, preferably a central processing unit (CPU) including calibration routine software and other computer hardware and software. Alternatively, all calibration routine software and hardware can be included in one or more components of system 100, such as the interface included in central implant 135, and calibration apparatus 115 simply include a monitor, input device and communication means to transfer data with central implant 135. Shown in FIG. 3, calibration apparatus 115 communicates with central implant 135 via wireless communication, transcutaneous communication means 160.

System 100 may include integrated memory storage for storing any and all data collected during the calibration process. This stored memory can be used for a number of functions including a second calibration procedure performed off line and/or away from the patient. This remote calibration, under different conditions, may allow an enhanced calibration procedure to be performed on a different time scale or with different equipment. If applicable, the new calibration output parameters could be implemented at a later date, either remotely or at the patent's site.

The calibration monitors described, such as calibration monitor 120, can display information separately for each electrode, as well as separately for each multicellular signal even if multiple signals are received from a single electrode. Also displayed can be the timing of patient events, such as the start and stop of imagined motions, with time adjustable windows surrounding the neural signal activity pre and post the time of the patient event. These window times could be adjusted by the operator. Real time and cumulative calibration information can be displayed including spatial representations of data, such as that relative to the geometric construction of an electrode array. For ease of use, color schemes can accompany numeric output to indicate various neural signal parameters such as firing rates of neuron spikes. Alternatively or additionally, calibration apparatus 115 may include output devices in addition to calibration monitor 120, such as audio devices or tactile devices, that can be used by the operator or the patient during calibration. While searching for multicellular signals with high firing rate, audio feedback may be used to sort signals with the highest rates.

The interface of system 100 may be comprised of various functions including an integrated neuron spike sorting function. This sorting function may include a method of sorting that includes setting a minimum signal amplitude threshold. The calibration routine may be as automated as possible. Due to the critical nature of these type of devices, it may be practical not to eliminate all involvement of the clinician and appropriate healthcare professionals. In an embodiment, the calibration routine of system 100 includes one or more automated calibration steps, and the operator performs a limited, but critical function. Such critical function may include one or more of: initiation of the calibration routine, confirmation of acceptable completion of the calibration routine, safety and/or performance check of the new calibration output parameters, or other confirmatory step to prevent an adverse event resulting from an improper automated calibration.

Numerous algorithms, mathematical and software techniques can be utilized by the interface to create the desired control signal. The interface may utilize neural net software routines to map neural signals into desired device control signals. Individual neural signals may be assigned to a specific use in the system. The specific use may be determined by having the patient attempting an imagined movement or other imagined state. For some applications, the neural signals may be under the voluntary control of the patient. The interface may mathematically combine various neural signals to create a processed signal for device control.

Figure 4:
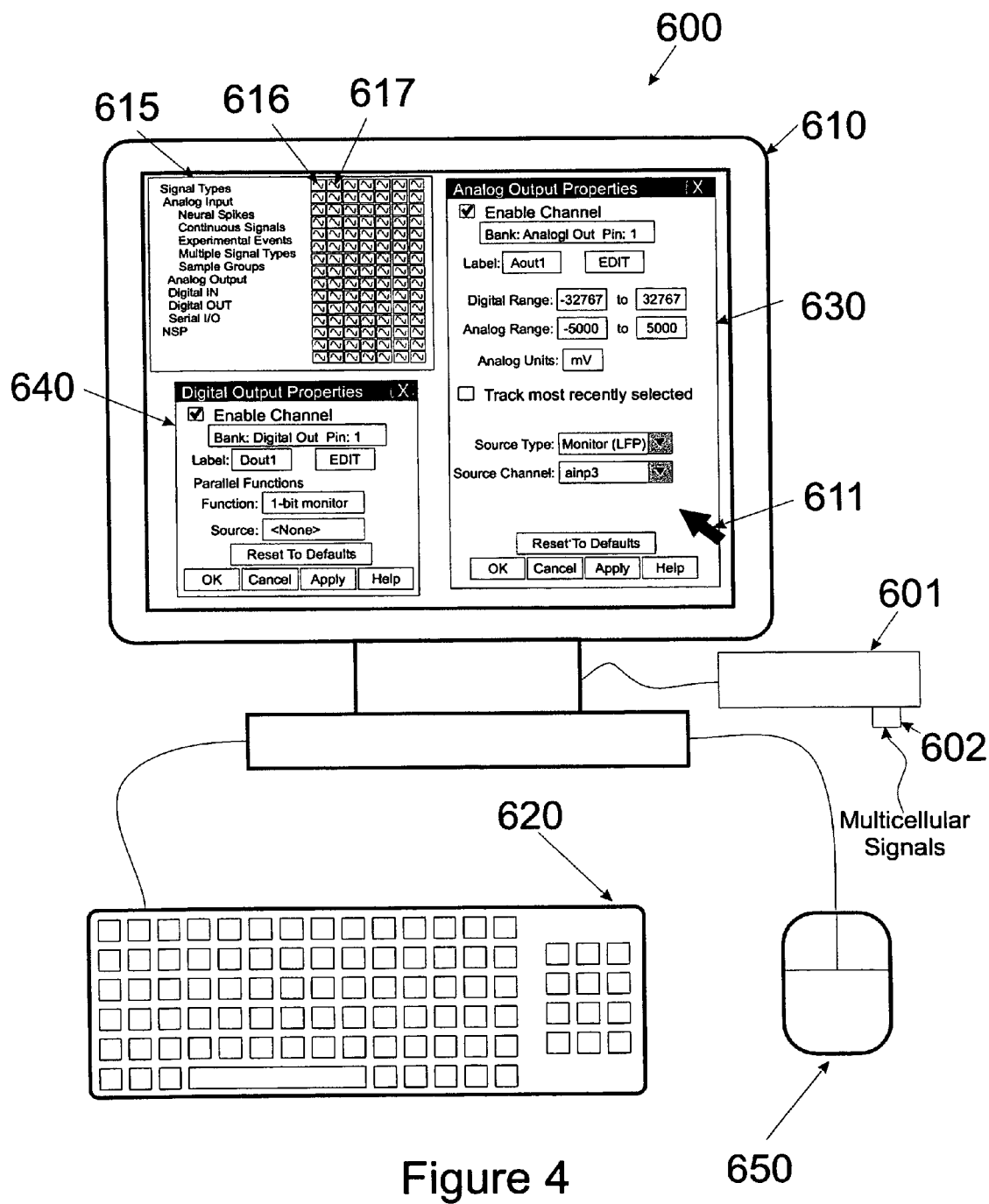
FIG. 4 illustrates an exemplary embodiment of a neural signal processing unit consistent with the present invention.

Referring now to FIG. 4, a neural signal processing unit 600 is depicted for processing of neural signals. Neural signal processing can include one or more of: amplifying, filtering, translating, identifying, classifying, sorting, conditioning, interpreting, encoding, decoding, combining, extracting, providing analog representations, providing digital representations, mathematically transforming and/or otherwise processing neural signals. Neural signal processing unit (NSPU) 600 includes a central processing unit (CPU) 601 which is attached to NSPU display 610, NSPU Mouse 650 and NSPU Keyboard 620. NSPU CPU 601 may include all computer functions including hardware and software elements to perform the neural signal processing. NSPU 600 includes an input port 602 (e.g., sensor input port) which can be attached directly to a multicellular signal sensor or to an intermediate device which carries processed multicellular singles, such as amplified multicellular signals. Additional input devices, such as a joystick and output devices, such as a speaker, can be attached to NSPU CPU 601 to aid an operator in the use of the NSPU 600.

Displayed on NSPU display 610 are various windows of information. NSPU channel list window 615 displays various channels of information correlating to specific electrodes of a multicellular signal sensor. Alternatively, each channel may display a specific multicellular signal or a group of specific electrodes or specific multicellular signals. Included in NSPU channel list window 615 is information about all channels including NSPU channel one information 616 and NSPU channel two information 617. NSPU digital output properties window 640 includes various pieces of digital information associated with one or more channels. NSPU analog output properties window 630 includes various pieces of analog information associated with one or more channels. Also shown on NSPU display 610 is NSPU display cursor 611, which is controlled via NSPU mouse 650.

An operator, not shown, can select multiple channels of data input, each representing a specific electrode, a specific multicellular signal or a specific group of multicellular signals or multiple electrodes. Multiple channels are selected, such as NSPU channel one 616 and NSPU channel two 617, either with a combination of keystrokes or use of the mouse 650's click function or both. After selection of one or more channels, both NSPU digital output properties window 640 and NSPU analog output properties window 630 can display common properties between all channels selected. The operator, utilizing either NSPU digital output properties window 640 or NSPU analog output properties window 630, or both, can set individual properties to a specific value. The properties of multiple channels can then be changed to those values simultaneously such as by clicking the "APPLY" function shown in both windows, or via a particular keystroke on NSPU keyboard 620. The selection of multiple channels, as well as the setting of the specific property values, can be accomplished by using various techniques employed in standard computer operating systems. After the multiple channels are selected, the NSPU may allow rapid changing of properties to specific selectable values, avoiding the need to set each channel individually.

Figure 5:
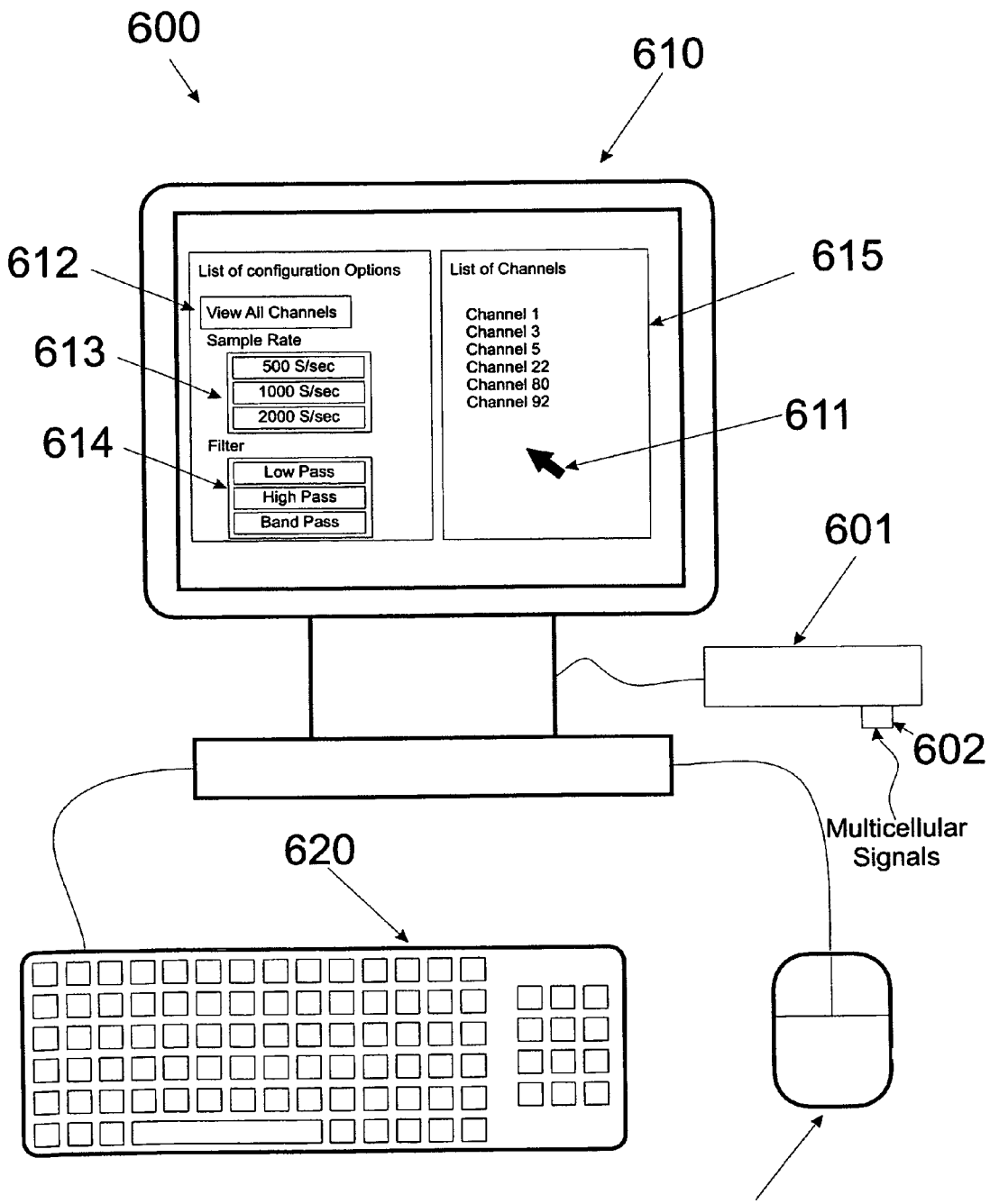
FIG. 5 illustrates another exemplary embodiment of a neural signal processing unit consistent with the present invention.

FIG. 5 shows an exemplary embodiment of a neural signal processing unit (NSPU) 600 for processing of neural signals. Neural signal processing can include one or more of: amplifying, filtering, translating, identifying, classifying, sorting, conditioning, interpreting, encoding, decoding, combining, extracting, providing analog representations, providing digital representations, mathematically transforming, and/or otherwise processing neural signals. NSPU 600 includes a central processing unit (CPU) 601 which is attached to NSPU display 610, NSPU Mouse 650 and NSPU Keyboard 620. NSPU CPU 601 may include all computer functions including hardware and software elements to perform the neural signal processing. Also shown on NSPU display 610 is NSPU display cursor 611, which is controlled via NSPU mouse 650. Neural signal processing unit 600 includes an input port 602 (e.g., sensor input port) which can be attached directly to a multicellular signal sensor or to an intermediate device which carries processed multicellular singles, such as amplified multicellular signals. Additional input devices, such as a joystick and output devices, such as a speaker, can be attached to NSPU CPU 601 to aid an operator in the use of the NSPU 600.

Displayed on NSPU display 610 are various windows of information. NSPU Option One button 612 is a mouse clickable button which allows the operator to view all channels. NSPU Option two 613 includes multiple clickable buttons that allow the user to select various sampling rates. NSPU Option three 614 includes multiple clickable button that allow the user to select various filtering parameters. NSPU Channel List 615 displays a list of applicable channels. In the embodiment of FIG. 5, the operator is provided with a powerful graphical user interface to find channels that have specific parameters and/or to easily change the parameters of individual or groups of channels. The operator can pick a particular parameter, such as a 500 S/sec sampling rate, and all channels sampled at that rate will appear in NSPU Channel list 615. Alternatively, a particular channel can be selected, and the parameters associated with that channel will appear.

The graphical user interface allows easy setting of parameters as mentioned above. The operator can use the mouse to select and drag any channel or group of channels to the screen location of a particular parameter value, and the channel will then be set to that value. Alternatively, the operator can select and drag any parameter value, or group of parameter values, to a screen location of a particular channel and the channel will have its parameter values automatically changed to those selected. It should be appreciated that while FIG. 5 depicts sampling rate and filter methods, any appropriate parameter value would be applicable to this embodiment. It should also be appreciated, that numerous methods of selecting channels utilizing, singly or in combination, a mouse, computer keyboard, touch screen or other input device, can be employed without departing from the spirit of the described embodiment.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of calibrating a neural interface system, comprising:
    detecting a set of multicellular signals emanating from a central nervous system of a patient using a sensor comprising a plurality of electrodes for chronic detection of the set of multicellular signals, while the patient imagines multiple movements;
    receiving the set of multicellular signals from the sensor on an interface and processing the set of multicellular signals to generate a processed signal, wherein the processing includes excluding a multicellular signal from the set of multicellular signals, and wherein the processed signal is generated using one or more calibration output parameters;
    transmitting the processed signal from the interface to a controlled device;
    receiving the processed signal on the controlled device, and entering into a lockout condition wherein the patient is prevented from controlling the controlled device prior to successfully completing the calibrating of the neural interface system and wherein a repeat calibration is required before the processed signals are transmitted to the controlled device.

2. The method of claim 1 wherein the patient imagines the movement of a part of the body.

3. The method of claim 1 further comprising comparing the multiple imagined movements to select the calibration output parameters.

4. The method of claim 1 further comprising categorizing the set of multicellular signals into three or more classifications for further processing into the processed signal for transmission to the controlled device.

5. The method of claim 1 wherein the detecting the set of multicellular signals is performed by a sensor having a two dimensional array of multiple protruding electrodes.

6. A method of calibrating a neural interface system, comprising:
    detecting a set of multicellular signals emanating from a central nervous system of a patient using a sensor comprising a plurality of electrodes for chronic detection of the set of multicellular signals, while the patient thinks of an imagined movement, imagined state, or imagined event;
    receiving the set of multicellular signals from the sensor on an interface and processing the set of multicellular signals to generate a processed signal, wherein the processing includes excluding a multicellular signal from the set of multicellular signals, and wherein the processed signal is generated using one or more calibration output parameters;
    transmitting the processed signal from the interface to a controlled device;
    receiving the processed signal on the controlled device, and entering into a lockout condition wherein the patient is prevented from controlling the controlled device prior to successfully completing the calibrating of the neural interface system and wherein a repeat calibration is required before the processed signals are transmitted to the controlled device.

7. The method of claim 6 wherein the patient imagines an emotion.

8. The method of claim 6 wherein the patient imagines a thought of being hot or cold.

9. A method of calibrating a neural interface system, comprising:
    using audio cues, visual cues, olfactory cues and tactile cues to trigger a patient's imagination;
    detecting a set of multicellular signals emanating from a central nervous system of a patient using a sensor comprising a plurality of electrodes for chronic detection of the set of multicellular signals;
    receiving the set of multicellular signals from the sensor on an interface and processing the set of multicellular signals to generate a processed signal, wherein the processing includes excluding a multicellular signal from the set of multicellular signals, and wherein the processed signal is generated using one or more calibration output parameters;
    transmitting the processed signal from the interface to a controlled device;
    receiving the processed signal on the controlled device, and entering into a lockout condition wherein the patient is prevented from controlling the controlled device prior to successfully completing the calibrating of the neural interface system and wherein a repeat calibration is required before the processed signals are transmitted to the controlled device.

10. The method of claim 9 wherein calibrating comprises:
    setting a preliminary set of calibration output parameters;
    using the preliminary set of calibration output parameters to generate the processed signal;
    measuring the performance of the controlled device; and
    modifying the calibration output parameters.

11. The method of claim 9 further comprising using one or more calibration input parameters to determine the calibration output parameters.

12. The method of claim 9 further comprising categorizing the set of multicellular signals into three or more classifications for further processing into the processed signal for transmission to the controlled device.

13. The method of claim 9 wherein the detecting the set of multicellular signals is performed by a sensor having a two dimensional array of multiple protruding electrodes.

14. The method of claim 9 wherein the calibration output parameters are set within preset limits.

15. The method of claim 9 further comprising using one or more calibration input parameters to determine the calibration output parameters.

16. The method of claim 9 further comprising categorizing the set of multicellular signals into three or more classifications for further processing into the processed signal for transmission to the controlled device.

17. The method of claim 9 further comprising storing the calibration output parameters in memory.

18. The method of claim 9 further comprising displaying signals received from the sensor on a display monitor.

* * * * *